United States Patent [19]

Haber et al.

[11] 4,224,448
[45] Sep. 23, 1980

[54] 2'-(5'-NITROFURYL) SUBSTITUTED QUINOLINES

[76] Inventors: Raphael R. G. Haber, 42, Kaplansky St., Givatayim, Israel; Eva Schoenberger, 38 Mivza Sinai St., Bat-Yam, Ramat Yosef, both of Israel

[21] Appl. No.: 909,401

[22] Filed: Oct. 19, 1977

Related U.S. Application Data

[63] Continuation of Ser. No. 516,361, Oct. 21, 1974, abandoned, which is a continuation of Ser. No. 204,694, Dec. 3, 1971, abandoned, which is a continuation-in-part of Ser. No. 643,830, Jun. 6, 1967, Pat. No. 4,087,427.

[30] Foreign Application Priority Data

Jun. 23, 1966 [IL] Israel .................................... 26022

[51] Int. Cl.$^2$ .................... A61K 31/47; C07D 215/00
[52] U.S. Cl. .................................... 546/167; 424/258; 424/248.4; 544/128; 546/101; 546/110; 546/153; 546/157
[58] Field of Search ........ 260/289 R, 288 CE, 283 R; 546/167, 101, 110, 153, 157

[56] References Cited

U.S. PATENT DOCUMENTS

| 2,742,462 | 4/1956 | Geven ................................. 260/240 |
| 3,157,645 | 11/1964 | Spencer ............................... 260/240 |
| 3,272,828 | 9/1966 | Von Esch et al. ............. 260/287 CE |
| 3,349,095 | 10/1967 | Haber et al. ................. 260/347.8 C |
| 3,352,683 | 11/1967 | Schmidt et al. ................. 260/240 X |
| 3,374,239 | 3/1968 | Burch .............................. 260/287 R |
| 3,475,421 | 10/1969 | Chretren et al. ................ 260/289 R |
| 3,496,066 | 2/1970 | Berger et al. .................... 260/289 R |

FOREIGN PATENT DOCUMENTS

| 1443177 | 9/1966 | France .................................. 260/347.8 |
| 6708540 | 12/1967 | Netherlands ............................. 260/288 |

Primary Examiner—Donald G. Daus
Assistant Examiner—James H. Turnipseed
Attorney, Agent, or Firm—Ostrolenk, Faber, Gerb & Soffen

[57] ABSTRACT 2- and 4- (5'nitrofuryl) quinoline derivatives which may be variously substituted on the quinoline nucleus have been found to possess excellent antibacterial and antifungal activity. Procedures for their manufacture are disclosed.

26 Claims, No Drawings

2'-(5'-NITROFURYL) SUBSTITUTED QUINOLINES

This is a continuation of application Ser. No. 516,361, filed Oct. 21, 1974 now abandoned which was a continuation of application Ser. No. 204,694 filed Dec. 3, 1971 and now abandoned, which was a continuation-in-part of Ser. No. 643,830, filed June 6, 1967 now U.S. Pat. No. 4,087,427.

The present invention relates to new nitrofuryl quinoline derivatives, to processes for their preparation and to compositions containing said derivatives.

The quinoline derivatives of the invention are substituted in either the 2- or 4-position by a 5-nitrofuryl group, and may be further substituted; and the invention includes further the nitrogen oxides and non-toxic acid addition salts of said derivatives.

Suitable substitutents with which the new nitrofuryl quinolines according to the present invention may be substituted are, for example, lower alkyl ($C_1$–$C_5$) radicals, branched or unbranched, which may be further substituted, e.g. by halogen atoms (preferably chlorine and bromine); lower alkoxy ($C_1$–$C_5$) radicals; hydroxy; carboxy; acyloxy; acyloxy-lower alkyl and hydroxy lower alkyl; nitro groups; halogen atoms; aldehydo and keto carbonyl groups, their oximes and hydrazones; amino groups which may be further substituted, e.g. by substituted or unsubstituted lower alkyl radicals, or by acyl radicals; cycloalkyl radicals; and carboxy and sulfonic acid groups and their esters and amides. Moreover, the 6- and 7-carbon atoms may together be part of a further aromatic or heteroaromatic nucleus which may itself be substituted.

Valuable nitrofuryl quinoline derivatives according to the present invention are, for example, compounds of the general formula I

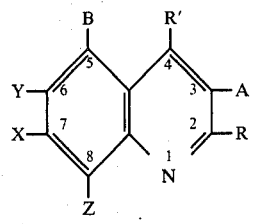

in which R stands for hydrogen, a 5-nitrofuryl group, a substituted, as by halogen and hydroxy, or unsubstituted lower alkyl radical of 1 to 5 carbon atoms, branched or unbranched, an acyloxy- or hydroxy-lower alkyl, such as methyl, group; an aldehydo or keto carbonyl group, its oxime or one of its hydrazones; and a carboxyl group or one of its esters or amides, including carboxy, carbethoxy, and carboxylic acid alkyl amides and N-morpholine and other cyclic nitrogen amides; R' stands for hydrogen, a 5-nitrofuryl group, lower alkyl, an acyloxy, such as lower alkanoyloxy, lower alkanoyloxylower alkyl, hydroxy-lower alkyl, a keto or aldehydo carbonyl group, its oxime or one of its hydrazones, or a substituted or unsubstituted lower alkyl- or amino radical, X stands for hydrogen, a halogen atom, a hydroxy or acyloxy group, particularly a lower alkanoyloxy group, a lower alkoxy radical, such as methoxy and butoxy (preferably n-butoxy), a substituted or unsubstituted lower alkyl or a substituted or unsubstituted amino radical, such as lower alkylamino and lower alkanoylamido; Y stands for hydrogen, for a substituted or unsubstituted lower alkyl radical, branched or unbranched, or a free or substituted amino, as by a lower alkyl or an acyl group; Z stands for hydrogen, a halogen atom, preferably chlorine or bromine, a nitro group or a substituted or unsubstituted, branched or unbranched, lower alkyl- or an amino radical, A stands for hydrogen or a substituted or unsubstituted lower alkyl radical, B stands for hydrogen, a nitro group or a substituted or unsubstituted amino radical, and X and Y taken together may constitute part of an aromatic or heteroaromatic nucleus, which may be further substituted, at least one of the substituents R or R' being a 5-nitrofuryl group.

The new nitrofuryl quinoline derivatives according to the present invention may be prepared by various processes. Some of them constitute also a part of the present invention.

Thus, certain of the new nitrofuryl quinoline derivatives bearing the 5-nitrofuryl group in the 4- position are prepared by the condensation of an 1-(5'-nitrofuryl)-1,3-diketobutane of the general formula II (described in U.S. Pat. No. 3,349,095 or French Pat. No. 1,443,177)

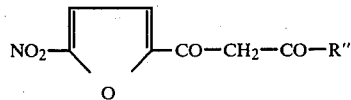

with a primary amine of general formula (III)

to yield an anil of general formula IV

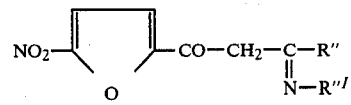

in which formulae R" stands for a substituted or unsubstituted lower alkyl radical and R"² stands for a substituted or unsubstituted phenyl radical, whereafter the anil compound of general formula IV is subjected to a ring closure treatment.

The condensation step is preferably carried out by either melting the reactants together in the presence of a catalyst, e.g. $ZnCl_2$ or by boiling said reactants together in an inert solvent, e.g. isopropanol. The anils of general formula IV are obtained by these methods in nearly theoretical yields.

The ring closure treatment is preferably carried out with concentrated sulfuric acid or with polyphosphoric acid at temperatures between 0 degrees and 180 degrees C.

The anils of general formula IV are also new compounds and constitute a part of the present invention.

Certain nitrofuryl quinoline derivatives bearing the 5-nitrofuryl group in 2- position are prepared by the condensation of a 5-nitrofuryl ketone of general formula V ("The Furans", by A. P. Dunlop and F. N. Peters, American Chemical Society Monograph Series, 1953, pages 429; 155)

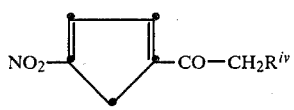

with a compound of general formula VI

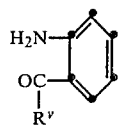

wherein the phenyl nucleus may be further substituted, in which formulae $R^{iv}$ stands for hydrogen or a substituted or unsubstituted lower alkyl radical and $R^v$ for hydrogen or a lower alkyl radical, in the presence of a catalyst, e.g. $ZnCl_2$, if desired, with the addition of a solvent, e.g. glacial acetic acid.

Further substituents may be introduced into the quinoline moiety in any suitable manner at any stage of the above or other processes. Eventually certain new nitrofuryl quinoline derivatives according to the present invention may be converted into other ones by methods known per se.

Thus, for example, alkyl radicals may be converted into halogenated alkyl radicals by way of halogenation, into a carbonyl group by way of oxidation, e.g. with selenium dioxide, or be converted into a carboxyl group by way of, for exmple, oxidation, which carboxyl group in turn may be esterified.

The carbonyl group may be converted into the oxime by reaction with hydroxylamine, and into a hydrazone by reaction with the appropriate hydrazine derivative.

The hydroxy group may be converted into the acyloxy group by way of esterification, and vice versa the acyloxy group may be converted into the hydroxy group, by way of hydrolysis.

The nitrofuryl quinoline derivatives according to the present invention may be ring-nitrated with concentrated nitric acid without destroying either the furan nucleus or the quinoline nuclei.

The nitrofuryl quinoline derivatives according to the present invention may be converted into the corresponding nitrogen-oxides, and acid-addition salts by methods known per se. Thus, the nitrogen-oxide is prepared by oxidation of the appropriate nitrofuryl quinoline derivative with a suitable peroxide, e.g. hydrogen peroxide, and the acid-addition salt by the reaction with an appropriate acid.

A suitable process for the preparation of nitrofuryl quinoline derivatives bearing in the 4- position the 5-nitrofuryl group and in the 2- position an acyloxy- or hydroxymethyl group, consists in reacting the 2-methyl-4-[2'-(5'-nitrofuryl)] quinoline N-oxide with a carboxylic acid anhydride and, if desired, subjecting the product obtained to hydrolysis.

The new nitrofuryl quinoline derivatives according to the present invention have excellent antibacterial properties. They are also active antifungal agents and are relatively non-toxic. They may be used as therapeutic agents in the veterinary field and as fungicides in agriculture. Due to the broad spectrum activity against various types of bacteria and fungi the compounds described may be used with advantage in the external treatment of wounds.

The pharmaceutical activity appears to be due to the combination of the quinoline with the directly linked 2- and 4-(5'-nitrofuryl) moieties and not primarily to the other non-toxic substituents indicated above; these other substituents on the quinoline molecule modify to varying degrees the basic activity of the 2- or 4-(5'-nitrofuryl)-quinoline but do not destroy it. We have found no compounds falling within the scope of the appended claims to be devoid of antimicrobial properties.

The activity of some of the new nitrofuryl quinoline derivatives of the present invention is exemplified in Table 1 against a gram-positive (*Staph. aureus*), a gram-negative (Salmonella) bacterium and a fungus (*Candida albicans*). Table 1 indicates the minimum inhibitory concentration of the compound under reference in mg/100 cc required in order to inhibit the growth between 1 and 6 strains of each type. The measurements have been carried out by the conventional tube dilution method at 37 degrees after 24 hours.

TABLE

| | | | | | | | Minimal Inhibitory Concentration in mg. % | | |
|---|---|---|---|---|---|---|---|---|---|
| R | A | R' | B | Y | X | Z | Staph. aureus | Salm. | Cand Alb. |
| NF | H | H | H | H | H | H | 0,05 | 2.5 | 0,2–0,5 |
| NF | H | $CH_3$ | H | H | H | H | 0,02–0,05 | 0,5 | 0,05 |
| H | H | NF | H | H | H | H | 0,01–0,05 | 0,5 | 0,1 |
| $CH_3$ | H | NF | H | H | H | H | 0,01–0,1 | 0,5 | 0,5 |
| $CH_3$ | H | NF | H | $CH_3$ | H | H | 0,01 | 0,5 | 0,5 |
| $CH_3$ | H | NF | H | $C_2H_5$ | H | H | 0,01 | 2,5 | 2,5 |
| $CH_3$ | H | NF | H | H | $CH_3$ | H | 0,005–0,01 | 0,2–0,5 | 0,3 |
| $CH_3$ | H | NF | H | H | OH | H | 0,01 | 0,5 | 1 |
| $CH_3$ | H | NF | H | H | $OCOCH_3$ | H | 0,005 | 0,2 | 1 |
| $CH_3$ | H | NF | H | H | $OCH_3$ | H | 0,025 | 1 | 0,5 |
| $CH_3$ | H | NF | H | H | $OC_2H_5$ | H | 0,01 | 0,5 | 2,5 |
| $CH_3$ | H | 5NF | H | H | $OC_4H_9$ | H | 0,05 | | >5 |
| $CH_3$ | H | NF | H | H | Cl | H | 0,01 | 0,05 | 2,5 |
| $CH_3$ | H | NF | H | H | H | $CH_3$ | 0,03 | >5 | 0,5 |
| $CH_3$ | H | NF | H | H | H | $C_2H_5$ | 0,005 | >5 | 10 |
| $CH_3$ | H | NF | H | $CH_3$ | H | $CH_3$ | 0,005–0,01 | >5 | >5 |
| $CH_3$ | H | NF | H | ⌿—\ | | H | 0,5 | >1 | >5 |
| $CH_3$ | H | NF | H | $OCH_3$ | $OCH_3$ | H | 0,05–0,1 | 2,5 | >5 |
| $CH_3$ | H | NF | H | $OC_4H_9$ | $OC_4H_9$ | H | 0,5 | 1 | >5 |
| $CH_3$ | H | NF | H | $NH_2$ | $OCH_3$ | H | 0,005 | 0,1–0,5 | 0,5 |
| $CH_3$ | H | NF | H | $NHCOCF_3$ | F | $OCH_3$ | 0,005 | >5 | >5 |
| $CH_3$ | H | NF | H | $NHCOCH_3$ | $OCH_3$ | H | 0,005 | >5 | 5 |

| | | | | | | | Minimal Inhibitory Concentration in mg. % | | |
|---|---|---|---|---|---|---|---|---|---|
| CH$_3$ | H | NF | H | COOH | OH | H | 1 | >5 | >5 |
| CH$_3$ | H | NF | H | H | NH$_2$ | CH$_3$ | 0,005 | 0,1-0,5 | 0,5 |
| CH$_3$ | H | NF | H | H | NHCOCH$_3$ | CH$_3$ | 0,1 | >5 | >5 |
| CH$_3$ | H | NF | H | H | NHCOCF$_3$ | CH$_3$ | 0,05 | >5 | >5 |
| CH$_3$ | H | NF | CH$_3$ | H | H | NH$_2$ | 0,5 | >5 | >5 |
| CH$_3$ | H | NF | OCH$_3$ | H | H | OCH$_3$ | 5 | >5 | >5 |
| CH$_3$ | H | NF | OCH$_3$ | H | OCH$_3$ | H | 0,05 | >5 | >5 |
| CH$_3$ | H | NF | NO$_2$ | H | H | CH$_3$ | 0,05-0,1 | >5 | >5 |
| C$_2$H$_5$ | H | NF | H | H | H | H | 0,01 | >5 | 0,5 |
| C$_2$H$_5$ | H | NF | H | CH$_3$ | H | H | 0,005 | >->1 | <0,5 |
| C$_2$H$_5$ | H | NF | H | C$_2$H$_5$ | H | H | 0,005 | >1 | >5 |
| C$_2$H$_5$ | H | NF | H | H | CH$_3$ | H | 0,5 | >5 | >5 |
| C$_2$H$_5$ | H | 5NF | H | H | OH | H | 0,01-0,05 | 0,5 | 5 |
| C$_2$H$_5$ | H | 5NF | H | H | OCH$_3$ | H | 0,001-0,05 | 2,5 | 1 |
| C$_3$H$_7$ | H | NF | H | CH$_3$ | H | H | 0,1 | >5 | 0,5-1 |
| C$_3$H$_7$ | H | NF | H | H | CH$_3$ | H | 0,5 | >5 | >5 |
| CH(CH$_3$)$_2$ | H | 5NF | H | C$_2$H$_5$ | H | H | 0,05 | | 5 |
| CH$_2$OH | H | NF | H | H | H | H | 0,01 | 0,5-1 | 0,5 |
| CH$_2$OCOCH$_3$ | H | NF | H | H | H | H | 0,005 | >5 | 0,5 |

| R$_1$R | A | R' | B | Y | X | Z | Staph. aureus | Salm. | Cand Alb. |
|---|---|---|---|---|---|---|---|---|---|
| CH$_2$OCOCH$_3$ | H | NF | H | H | OCOCH$_3$ | H | 0,005 | 1-2,5 | 5-10 |
| CBr$_3$ | H | NF | H | H | H | H | 0,05 | 1 | 3-5 |
| CBr$_3$ | H | NF | H | CH$_3$ | H | H | 0,1 | >2,5 | >5 |
| CH(OAc)$_2$ | H | NF | H | H | H | H | 0,01 | 0,5 | 2,5-5 |
| CH=NOH | H | NF | H | H | H | H | 0,005 | 0,5 | 1 |
| CH=NOH | H | NF | H | H | OC$_2$H$_5$ | H | 0,005 | >5 | 5 |
| CH=N—NH—CH$_3$ | H | NF | H | H | H | H | 0,005 | 0,1-0,5 | 1-2,5 |
| CH=N—NHCONH$_2$ | H | NF | H | H | H | H | 0,005 | 0,5 | 2,5-5 |
| CH=N—NH—HOCH$_2$—CH$_2$ | H | NF | H | H | H | H | 0,005 | 0,5 | 2,5 |
| CH=N—N(CO—O)(CH$_2$—CH$_2$) | H | NF | H | H | H | H | 0,01-0,05 | 5->5 | 0,5 |
| COCH$_3$ | H | NF | H | H | H | H | 0,001 | >5 | >5 |
| COOH | H | NF | H | H | H | H | 0,1 | >1 | 3-5 |
| COOH | H | 5NF | H | H | CH$_3$ | H | 0,05 | 2,5 | 5 |
| COOH | H | 5NF | H | H | OCH$_3$ | H | 0,05 | 1 | 5 |
| COOH | H | NF | H | H | OC$_2$H$_5$ | H | 0,05 | 0,5 | >5 |
| COOC$_2$H$_5$ | H | NF | H | H | H | H | 0,005 | >5 | >5 |
| CON(C$_2$H$_5$)$_2$ | H | NF | H | H | H | H | 0,05-0,1 | >5 | >5 |
| CO—N(CH$_2$CH$_2$)$_2$O | H | NF | H | H | H | H | 0,01-0,05 | 2,5-5 | 5 |
| CH$_2$—CHOH—CCl$_3$ | H | NF | H | H | H | H | 0,05 | >5 | >5 |
| O NF | H | H | H | H | H | H | 0,05 | 1 | <0,5 |
| O NF | H | CH$_3$ | H | H | H | H | 0,1 | 1 | 0,2-0,5 |
| O H | H | NF | H | H | H | H | 0,01-0,05 | 0,5 | 0,05 |
| O H | H | NF | H | H | OCH$_3$ | H | 0,001-0,005 | 0,5 | 0,05 |
| O CH$_3$ | H | NF | H | H | H | H | 0,02-0,05 | 1 | 0,1 |
| O CH$_3$ | H | NF | H | CH$_3$ | H | H | 0,01 | >2,5 | 0,2-0,5 |
| O CH$_3$ | H | NF | H | C$_2$H$_5$ | H | H | 0,05 | 2,5 | 0,2-0,5 |
| O CH$_3$ | H | NF | H | H | CH$_3$ | H | 0,005 | >5 | 0,5 |
| O CH$_3$ | H | NF | H | H | OH | H | 0,005 | 0,5-1 | 10 |
| O CH$_3$ | H | NF | H | H | OCOCH$_3$ | H | 0,005 | 0,5 | 5 |
| O CH$_3$ | H | NF | H | H | OCH$_3$ | H | 0,01 | 0,5 | 0,05 |
| O CH$_3$ | H | NF | H | H | OC$_2$H$_5$ | H | 0,005-0,01 | 1-5 | 1 |
| O CH$_3$ | H | NF | H | H | OC$_4$H$_9$ | H | 0,05-0,1 | | >1 |
| O CH$_3$ | H | NF | H | H | Cl | H | 0,1 | >2,5 | 0,2-0,5 |
| O CH$_3$ | H | NF | H | | | H | 0,05-0,1 | >5 | 5 |
| O CH$_3$ | H | NF | H | OCH$_3$ | OCH$_3$ | H | 0,005 | >5 | >5 |
| O CH$_3$ | H | NF | H | NH$_2$ | OCH$_3$ | H | 0,005 | 5 | >5 |
| O CH$_3$ | H | NF | H | NHCOCH$_3$ | OCH$_3$ | H | 0,005 | 1-2,5 | 5 |
| O C$_2$H$_5$ | H | NF | H | H | H | H | 0,03 | 2,5-5 | 0,3 |
| O C$_2$H$_5$ | H | NF | H | CH$_3$ | H | H | 0,01 | | <0,5 |
| O C$_2$H$_5$ | H | NF | H | C$_2$H$_5$ | H | H | 0,01 | >1 | 0,5-1 |
| O C$_2$H$_5$ | H | NF | H | H | CH$_3$ | H | 0,05 | 2,5-5 | <0,5 |

TABLE-continued

| | | | | | | | \multicolumn{3}{c}{Minimal Inhibitory Concentration in mg. %} |
|---|---|---|---|---|---|---|---|---|---|
| O C$_2$H$_5$ | H | NF | H | H | OH | H | 0,001 | 0,5 | 2,5 |
| O C$_2$H$_5$ | H | NF | H | H | OCH$_3$ | H | 0,001–0,05 | | >5 |
| O C$_3$H$_7$ | H | NF | H | CH$_3$ | H | H | 0,1–0,5 | >5 | 0,5–2,5 |
| OC$_3$H$_7$ | H | NF | H | H | CH$_3$ | H | 0,1 | >5 | >5 |
| O C$_3$H$_7$ | H | NF | H | C$_2$H$_5$ | H | H | 0,1 | >5 | >5 |
| O CH=NOH | H | NF | H | H | H | H | 0,005 | 0,1–0,5 | 0,05 |
| O COOH | H | NF | H | H | H | H | 0,05 | 5 | 1–2,5 |
| O COOH | H | NF | H | H | CH$_3$ | H | 0,05 | | 5 |
| R$_2$ = CO—N O | H | NF | H | H | H | H | 0,05–0,1 | 1–2,5 | 2,5–5 |
| R$_2$ = CH$_2$—CHOCH—CHCl$_3$ | H | NF | H | H | H | H | 0,05 | 1–5 | 5–>5 |

NF = 2'-(5'-nitrofuryl)
R$_1$ = O whenever indicated, i.e. it then refers to the N-oxide The new nitrofuryl quinoline derivatives according to the present invention may be prescribed to be taken per se, but are preferably prescribed in the form of tablets, capsules, ampules, ointments, tinctures or solutions, said preparations being prepared in a conventional manner, i.e. by the addition of suitable excipients, binders, extenders, emulsifiers, solvents, other suitable therapeutic compounds, and the like.

The new nitrofuryl quinoline derivatives of the present invention may also be used as feed additives. They may be either admixed directly with the feed, advantageously in an amount of about 0.001–1% of the total feed or as part of a pre-mix. Such pre-mix may contain, besides the nitrofuryl quinoline derivative, any suitable carrier and/or feed additive, e.g. bentonite, CaCO$_3$, soyabean meal, corn meal and the like. The pre-mix should contain about 1–95% of the new compound.

The invention will be illustrated by the following Examples without being limited by them. All temperatures are indicated herein in degrees Centigrade. All melting points are uncorrected.

EXAMPLE 1

5.91 g (0.03 mole) of 1-(5'-nitrofuryl)-butane-1,3-dione and 2.8 g (0.03 mole) of freshly distilled aniline were heated together at 120° with a catalytic amount of ZnCl$_2$. A clear melt was obtained and after 15 minutes the whole mass solidified. The melt was kept for a further 10 minutes at 120°. Thereafter it was cooled and recrystallised from methanol to yield 7.4 g of crystaline 1-(5'-nitro-2'-furo)-butanone-3-phenyl-imino of m.p. 127.5°–128.5°. Yield 87.5%.

Then, 5.6 g (0.02 mole) of the above Schiff base were dissolved at about 5° in 30 g of concentrated sulfuric acid. The clear solution obtained was allowed to reach room temperature, was thereafter heated for 10 minutes to 100°–110° and then poured on ice water.

An olivegreen precipitate was obtained which was filtered off and suspended in water. Ammonia was added to the suspension until the pH was slightly alkaline. The suspension was cooled and the precipitate obtained was filtered off to yield 2.4 g of 2-methyl-4-[2'-(5'-nitrofuryl)] quinoline, m.p.-127°–130°. Further ammonia was added to the mother liquor to yield a further 0.3 g of the above compound.

An analytical sample was obtained by recrystallisation from isopropanol/water; m.p. 138°–139°. The analysis was calculated for C$_{14}$H$_{10}$N$_3$O$_3$:

Calculated: C: 66.14%; H: 3.96%; N: 11.02%; Found: C: 66.08%; H: 4.10%, N: 10.98%.

2.7 g of the above quinoline derivative were dissolved with heating in 70 ml of glacial acetic acid, 2 ml of 30% hydrogen peroxide were added at once to the solution obtained, which was kept at 70° for 3 hours. The water was added and the resulting precipitate was filtered off to yield 2.4 g of 2-methyl-4-[2'-(5'-nitrofuryl)] quinoline N-oxide, m.p. 207°.

An analytical sample was prepared by recrystallisation from isopropanol and nitromethane; m.p. 226°–227°. The analysis was calculated for C$_{14}$H$_{10}$N$_2$O$_4$:

Calculated: C: 62.22%; H: 3.73%; N: 10.37%; Found: C: 62.47%; H: 3.69%; N: 10.29%.

The hydrochloride of 2-methyl-4-[2'-(5'-nitrofuryl)] quinoline has a m.p. of 190°–191.5°. The corresponding hydrobromide has a m.p. of 230.5°–231°.

EXAMPLE 2

3 g (0.02 mole) of 5-nitrofuryl methyl ketone and 2.7 g (0.02 mole) of o-amino acetophenone were heated together with a catalytic amount of ZnCl$_2$ at 150°, The clear melt obtained was heated for 1 hour at 140°–150°, then cooled and dissolved in isopropanol. The solution was filtered through charcoal. The filtrate was concentrated and cooled to yield 1.53 g (30%) of 2-[2'-(5'-nitrofuryl)]-4-methyl quinoline, m.p. 148°–162°.

An analytical sample was obtained by consecutive recrystallisation from acetone, isopropanol and benzene/petrol-ether; m.p. 167°–168°. The analysis was calculated for C$_{14}$H$_{10}$N$_2$O$_3$:

Calculated: C: 66.14%; H: 3.96%; N: 11.02%; Found: C: 65.94%; H: 4.14%; N: 10.98%.

The N-oxide has a m.p. of 210°–212°.

EXAMPLE 3

5.91 g (0.03 mole) of 1-(5'-nitrofuryl)-2,4-butanedione and 3.82 g (0.03 mole) of m-chloroaniline were melted together with a catalytic amount of ZnCl$_2$ in an open vessel at 110°–120°. After 10 minutes the heating was stopped, the mixture was cooled and dissolved in nitromethane. The solution obtained was filtered hot and the filtrate yielded after cooling 8.9 g (97% yield) of crystalline 1-(5'-nitro-2'-furo) butanone-3-(m-chlorophenyl) imino, m.p. 161°–162°.

6 g of the above enamine are added gradually with cooling to 18 ml of cooled concentrated sulfuric acid. The mixture was allowed to reach room temperature and then heated for 10 minutes to 100°–110°. The mixture was then cooled and poured on ice-water. The amorphous precipitate obtained was filtered off, washed with water, re-suspended in water and the suspension was made alkaline with ammonia to yield 5.5 g (yield 97%) of 2-methyl-4-[2'-(5'-nitrofuryl)]-7-chloro quinoline.

An analytical sample was prepared by recrystallisation from isopropanol and acetone/water; m.p. 146°. The analysis was calculated for $C_{14}H_9N_3O_3Cl$:

Calculated: C: 58.23%; H: 3.14%; N: 9.70%; Cl: 12.30%; Found: C: 58.33%; H: 3.08%; N: 9.53%; Cl: 12.26%.

1.2 g of the above quinoline derivative were dissolved with heating in 25 ml of glacial acetic acid. 2 ml of 30% hydrogen peroxide were added to the solution which was kept for 5 hours at 70°. Water was added and the precipitate obtained was filtered off to yield 1.15 g (yield 91%) of 2-methyl-4-[2'-(5'-nitrofuryl)]-7-chloro-quinoline N-oxide, m.p. 198°–204°.

An analytical sample was prepared by recrystallisation from nitromethane; m.p. 205°–206°. The analysis was calculated for $C_{14}H_9N_2O_4Cl$:

Calculated: C: 55.20%; H: 2.98%; N: 9.19%; Found: C: 55.15%; H: 3.09%; N: 9.13%.

EXAMPLE 4

5.91 g (0.03 mole) of 1-(5'-nitrofuryl)-2,4-butanedione and 3.9 g (0.03 mole) of m-aminophenol were heated together with a catalytic amount of $ZnCl_2$ at 90°. The clear melt so obtained was heated for 10 minutes at 100°–110°, then cooled and recrystallised from methanol to yield 6.1 g of 1-(5'-nitro-2'-furo)-butanone-3-(m-hydroxy-phenyl)imino; m.p. 190.5°–192°.

6 g of the above Schiff base were dissolved in 36 g of sulfuric acid at about 5°. The reaction mixture was kept for 5 days at room temperature and then poured on ice-water. The obtained aqueous suspension was neutralised with ammonia and the precipitated crystals were filtered off and recrystallised from ethanol to yield bright-yellow crystals of 2-methyl-4-[2'-(5'-nitrofuryl)]-7-hydroxy quinoline; m.p. 259°.

An analytical sample was obtained by repeated recrystallisation from ethanol and nitromethane; m.p. 272° (decomp.). The analysis was calculated for $C_{14}H_{10}N_2O_4$:

Calculated: C: 62.22%; H: 3.73%; N: 10.37%; Found: C: 62.03%; H: 3.92%; N: 10.20%.

2-Methyl-4-[2'-(5'-nitrofuryl)]-7-hydroxy quinoline N-oxide was prepared by oxidation of the above compound with $H_2O_2$ (30%) in glacial acetic acid. M.p. 293° (decomp). The analysis was calculated for $C_{14}H_{10}N_2O_5$:

Calculated: C: 58.75%; H: 3.52%; N: 9.79%; Found: C: 58.88%; H: 3.59%; N: 9.80%.

When the 2-methyl-4-[2'-(5'-nitrofuryl)]-7-hydroxy quinoline was O-alkylated with n-butyl bromide dissolved in acetone there was obtained 2-methyl-4-[2'-(5'-nitrofuryl)]-7-n-butoxy quinoline; m.p. 69°–70°.

When the O-alkylation is performed with iso-butyl bromide there is obtained 2-methyl-4-[2'-(5'-nitrofuryl)]-7-i-butoxy quinoline, m.p. 65°–70°.

When the O-alkylation is performed with propyl bromide there is obtained 2-methyl-4-[2'-(5'-nitrofuryl)]-7-propyl quinoline, m.p. 132°–134°.

EXAMPLE 5

2 g of 2-methyl-4-[2'-(5'-nitrofuryl)]quinoline, prepared as described in Example 1, were dissolved with heating in 20 ml of glacial acetic acid. 4.0 g of anhydrous sodium acetate and thereafter 1.25 ml of bromine dissolved in some acetic acid were added at 70°–75°. The reaction mixture was then heated for 90°–95°, then cooled and the precipitate obtained was filtered off to yield 3.6 g (yield 92%) of yellow crystals of 2-tribromomethyl-4-[2'-(5'-nitrofuryl)]quinoline; m.p. 154°–155°.

An analytical sample was obtained by recrystallisation from isopropanol; m.p. 158°–160°. The analysis was calculated for $C_{14}H_7N_2O_3Br_3$:

Calculated: C: 34.25%; H: 1.44%; N: 5.70%; Br: 48.83%; Found: C: 34.38%; H: 1.45%; N: 5.90%; Br: 49.03%.

EXAMPLE 6

1.5 g of 2-tribromomethyl-4-[2'-(5'-nitrofuryl)]quinoline, prepared as described in Example 5, were dissolved in 50 ml of 50% sulfuric acid. Catalytic quantities of $FeCl_3$ were added to the solution obtained, which was then kept for 20 hours at 110–130°. The clear solution was cooled, water was added and the precipitate obtained was filtered off to yield 0.4 g of 2-carboxy-4-[2'-(5'-nitrofuryl)]quinoline; m.p. 190°–193°.

An analytical sample was obtained by recrystallisation from glacial acetic acid; m.p. 200°. The analysis was calculated for $C_{14}H_8N_2O_5$:

Calculated: C: 59.16%; H: 2.84%; N: 9.86%; Found: C: 59.21%; H: 2.85%; N: 9.52%.

EXAMPLE 7

5.91 g (0.03 mole) of 1-(5'-nitrofuryl)-2,4-butanedione and 3.7 g (0.03 mole) of m-anisine were heated together with a catalytic amount of $ZnCl_2$ for 10 minutes at 110°. After cooling and recrystallisation from methanol, 1-[5'-nitro-2'-furo)-butanone-3-(m-methoxy-phenyl)imino was obtained, yield 81%; m.p. 137°.

The above enamine was subjected to a ring closure treatment similar to that described in Example 1 to yield 2-methyl-4-[2'-(5'-nitrofuryl)]-7-methoxy quinoline, yield 54%; m.p. 146°–148.5°.

An analytical sample was obtained by recrystallisation from isopropanol; m.p. 156°–157°. The analysis was calculated for $C_{15}H_{12}N_2O_4$:

Calculated: C: 63.38%; H: 4.25%; N: 9.85%; Found: C: 63.25%; H: 4.38%; N: 9.83%.

The N-oxide was prepared by oxidation with $H_2O_2$; m.p. 207°–208°.

EXAMPLE 8

19.7 g (0.1 mole) of 1-(5'-nitrofuryl)-2,4-butanedione and 10.7 g (0.1 mole) of p-toluidine were heated together with a catalytic amount of $ZnCl_2$ at 120°. After 10 minutes of further heating and working up as described in Example 1, 1-(5'-nitro-2'-furo)-butanone-3-(p-methyl-phenyl)imino was obtained, yield 98%, m.p. 145°–146°.

The above enamine was subjected to a ring closure treatment similar to that described in Example 1 to yield 2-methyl-4-[2'-(5'-nitrofuryl)]-6-methyl quinoline, yield 97%; m.p. 146°–148°.

An analytical sample was prepared by recrystallisation from isopropanol; m.p. 151°. The analysis was calculated for $C_{15}H_{12}N_2O_3$:

Calculated: C: 67.12%; H: 4.51%; N: 10.44%; Found: C: 67.08%; H: 4.57%; N: 10.57%.

The N-oxide was prepared by oxidation with $H_2O_2$; m.p. 227°–229° (after recrystallisation). The analysis was calculated for $C_{15}H_{12}N_2O_4$:

Calculated: C: 63.38%; H: 4.25%; N: 9.85%; Found: C: 63.60%; H: 4.41%; N: 9.74%.

EXAMPLE 9

2.8 g (0.01 mole) of 2-methyl-4-[2'-(5'-nitrofuryl)]-7-chloro quinoline, prepared as described in Example 3, were added gradually with cooling to 8 ml of concentrated sulfuric acid, the temperature being maintained below 0°. 0.6 ml of nitric acid (100%) was added in one portion to the mixture at said temperature. The mixture was then allowed to reach room temperature, kept at said temperature for 3 hours and then poured on ice-water. The amorphous precipitate obtained was filtered off, washed with water and dissolved in ethanol. The solution so obtained was filtered with charcoal, concentrated and cooled to yield 1.1 g of 2-methyl-4-[2'-(5'-nitrofuryl)]-7-chloro-8-nitro quinoline; m.p. 198°–202°.

An analytical sample was obtained by recrystallisation from isopropanol and nitromethane; m.p. 207°–208°. The analysis was calculated for $C_{14}H_8N_3O_5Cl$:

Calculated: C: 50.39%; H: 2.42%; Cl: 10.63%; Found: C: 50.15%; H: 2.51%; Cl: 10.43%.

There was similarly prepared 2,8-dimethyl-4-[2'-(5'-nitrofuryl]-5-nitroquinoline, m.p. 229°–232°.

EXAMPLE 10

Performing the process as described in Example 8, but replacing the p-toluidine by o-toluidine, 1-(5'-nitro-2'-furo)-butanone-3-(o-methyl-phenyl)imino was obtained; yield 91.5%; m.p. 127°–129°.

The enamine was subjected to a ring closure treatment similar to that described in Example 1 to yield 2,8-dimethyl-4-[2'-(5'-nitrofuryl)]quinoline, yield 82%; m.p. 147°–149°.

An analytical sample was obtained by recrystallisation from isopropanol and nitromethane; m.p. 157°–158.5°. The analysis was calculated for $C_{15}H_{12}N_2O_3$:

Calculated: C: 67.12%; H: 4.51%; N: 10.44%; Found: C: 67.05%; H: 4.36%; N: 10.52%.

The N-oxide of the above compound was prepared by oxidation with peracetic acid in glacial acetic acid. The melting point of the crude compound was 149°–151°.

An analytical sample was prepared by recrystallisations from isopropanol, yielding a compound melting at 158°–160°.

The analysis was calculated for $C_{15}H_{12}N_2O_4$:

Calculated: C: 63.38%; H: 4.25%; Found: C: 63.59%; H: 4.43%.

EXAMPLE 11

Performing the process as described in Example 8, but replacing the p-toluidine by m-toluidine, 1-(5'-nitro-2'-furo)-butanone-3-(m-methyl-phenyl)imino was obtained; yield 90.5%; m.p. 146°–147.5°.

The enamine was subjected to a ring closure treatment similar to that described in Example 1 to yield 2,7-dimethyl-4-[2'-(5'-nitrofuryl)]quinoline, yield 75%; m.p. 142°–145°.

An analytical sample was obtained by recrystallisation from isopropanol and nitromethane; m.p. 145°–146°. The analysis was calculated for $C_{15}H_{12}N_2O_3$:

Calculated: C: 67.12%; H: 4.51%; N: 10.44%; Found: C: 67.04%; H: 4.45%; N: 10.67%.

The N-oxide of the above compound was prepared by an oxidation reaction with $H_2O_2$ in glacial acetic acid. Yield 92%, m.p. 210°–212°.

An analytical sample was prepared by recrystallisation from ethoxy ethanol and nitromethane; m.p. 217°–218.5°. The analysis was calculated for $C_{15}H_{12}N_2O_4$:

Calculated: C: 63.38%; H: 4.25%; N: 9.85%; Found: C: 63.22%; H: 4.41%; N: 10.07%.

EXAMPLE 12

1.27 g of 2-methyl-4-[2'-(5'-nitrofuryl)]quinoline, prepared as described in Example 1, was dissolved in 13 ml of hot acetic acid. 0.45 g of anhydrous sodium acetate was added to the solution and then 0.8 g of bromine dissolved in 2 ml of acetic acid was added dropwise in the course of 15 minutes. The reaction mixture was then cooled and the crystals obtained filtered off. Thin layer chromatography showed that the material obtained was a mixture of 2-dibromo- and 2-tri-bromo-methyl-4-[2'-(5'-nitrofuryl)]quinoline.

The material was recrystallised in succession from ethanol, isopropanol, cellosolve and again isopropanol, to yield the dibromo-compound only; m.p. 187.5°–189°. The analysis was calculated for $C_{14}H_8N_2O_3Br_2$:

Calculated: C: 40.80%; H: 1.95%; N: 6.80%; Br: 38.90%; Found: C: 40.60%; H: 2.20%; N: 6.63%; Br: 38.64%.

EXAMPLE 13

2.54 g (0.01 mole) of 2-methyl-4-[2'-(5'-nitrofuryl)-]quinoline, prepared as described in Example 1, and 1.5 g of sodium carbonate were suspended in 80 ml of benzene. The mixture was heated to 70° and chlorine gas was bubbled therethrough in the course of 3 hours. After cooling, some unreacted starting material was filtered off and the filtrate was concentrated to yield 2-trichloromethyl-4-[2'-(5'-nitrofuryl)]quinoline; m.p. 142°–144°.

An analytical sample was obtained by recrystallisation from isopropanol and nitromethane; m.p. 145°–146°. The analysis was calculated for $C_{14}H_7N_2O_3Cl_3$:

Calculated: C: 47.02%; H: 1.98%; N: 7.83%; Cl: 29.73%; Found: C: 47.03%; H: 2.13%; N: 7.70%; Cl: 29.51%.

EXAMPLE 14

1.97 g (0.01 mole) of 1-(5'-nitrofuryl)-2,4-butanedione and 1.43 g (0.01 mole) of B-naphthylamine were heated together with a catalytic amount of $ZnCl_2$ for 10 minutes at 100°–110°. After cooling and recrystallisation 2.65 g (yield 82.5%) of 1-(5'-nitro-2'-furo)-butanone-3-naphthyl imino were obtained; m.p. 184°–186.5°.

The enamine obtained was heated with 6 times its weight of concentrated sulfuric acid for 10 minutes at 110°. After cooling the reaction mixture was poured on ice-water, neutralised and the precipitate obtained filtered off to yield 2-methyl-4-[2'-(5'-nitrofuryl)]-6,7-benzoquinoline; m.p. 221°.

An analytical sample was obtained by recrystallisation from nitromethane; m.p. 228°. The analysis was calculated for $C_{18}H_{12}N_2O_3$:

Calculated: C: 71.05%; H: 3.97%; N: 9.21%; Found: C: 71.21%; H: 3.96%; N: 8.98%.

The N-oxide was prepared by oxidation with $H_2O_2$ in glacial acetic acid, yield 98%, m.p. 230°–235°.

As analytical sample was prepared by recrystallisation from nitromethane, m.p. 241°–243°. The analysis was calculated for $C_{18}H_{12}N_2O_4$.

Calculated: C: 67.50%; H: 3.78%; N: 8.75%; Found: C: 67.33%; H: 3.94%; N: 8.76%.

EXAMPLE 15

2.7 g (0.01 mole) of 2-methyl-4-[2'-(5'-nitrofuryl)]-6-methyl quinoline, prepared as described in Example 8, were dissolved in 35 ml of acetic acid at 70°. At the same temperature were added 5.4 g of anhydrous sodium acetate and thereafter in the course of 25 minutes also 2.4 g of bromine dissolved in 5 ml of glacial acetic acid. The mixture was then heated for 1 hour at 90°–95°, then cooled and the formed precipitate was filtered off to yield 2.7 g of yellow-green crystals of 2-tribromomethyl-4-[2'-(5'-nitrofuryl)]-6-methyl quinoline; m.p. 191.5°–193°.

An analytical sample was obtained by recrystallisations from isopropanol, dioxane and nitromethane; m.p. 193°–195°. The analysis was calculated for $C_{15}H_9N_2O_3Br_3$:

Calculated: C: 35.60%; H: 1.78%; N: 5.54%; Br: 47.52%; Found: C: 35.74%; H: 2.03%; N: 5.35%; Br: 47.55%.

EXAMPLE 16

Performing the process as described in Example 2, but replacing the o-amino acetophenone with o-amino benzaldehyde, 2-[2'-(5'-nitrofuryl)]quinoline was obtained; m.p. 137°–147°.

An analytical sample was obtained by consecutive recrystallisation from methanol, isopropanol and ethoxy-ethanol; m.p. 196°–198°. The analysis was calculated for $C_{13}H_8N_2O_3$:

Calculated: C: 65.00%; H: 3.36%; N: 11.66%; Found: C: 64.82%; H: 3.32%; N: 11.92%.

The N-oxide had a m.p. of 215°–216°.

EXAMPLE 17

Performing the process as described in Example 2 but utilising as starting materials 5-nitrofuryl ethyl ketone and o-amino benzaldehyde, 2-[2'-(5'-nitrofuryl)]-3-methyl quinoline was obtained; m.p. 175°–196°.

EXAMPLE 18

2.54 g (0.01 mole) of 2-methyl-4-[2'-(5'-nitrofuryl)-]quinoline, prepared as described in Example 1, were added gradually with cooling to 8 ml of concentrated sulfuric acid, the temperature being maintained below 0°. 0.6 ml of nitric acid (100%) was added at said temperature in one portion. The mixture was then allowed to reach room temperature, kept at that temperature for 3 hours and then poured on ice-water. The precipitate obtained was filtered off, washed with water to yield 1.8 g of yellow crystals, m.p. 121°–157°.

Thin layer chromatography showed 2 spots corresponding to 2-methyl-4-[2'-(5'-nitrofuryl)]-5- and 8-nitro quinoline.

The recrystallised material had a m.p. of 193°–198°. The analysis was calculated for $C_{14}H_9N_3O_5$:

Calculated: C: 56.19%; H: 3.03%; Found: C: 56.36%; H: 3.04%.

EXAMPLE 19

In a manner similar to that described in Example 1 there were prepared:

a. 2-methyl-4-[2'-(5'-nitrofuryl)]-6-ethyl quinoline. m.p. 114°–115°. The analysis was calculated for $C_{16}H_{14}N_2O_3$:

Calculated: C: 68.08%; H: 5.00%; N: 9.92%; Found: C: 68.05%; H: 5.16%; N: 10.24%.

The corresponding N-oxide was prepared, m.p. 194°–195°. The analysis was calculated for $C_{16}H_{14}N_2O_4$:

Calculated: C: 64.42%; H: 4.73%; N: 9.39%; Found: C: 64.37%; H: 4.94%; N: 9.20%.

b. 2,6,8-trimethyl-4-[2'-(5'-nitrofuryl)]quinoline, m.p. 143°–143.5°. The analysis was calculated for $C_{16}H_{14}N_2O_3$:

Calculated: C: 68.08%; H: 5.00%; N: 9.92%; Found: C: 67.88%; H: 5.28%; N: 10.00%.

c. 2,5,8-trimethyl-4-[2'-(5'-nitrofuryl]quinoline, m.p. 133°–134°. The analysis was calculated for $C_{16}H_{14}N_2O_3$:

Calculated: C: 68.08%; H: 5.00%; N: 9.92%; Found: C: 68.39%; H: 4.91%; N: 9.72%.

d. 2-methyl-4-[2'-(5'-nitrofuryl)]-5,8-dimethoxy quinoline, m.p. 183°–183.5°. The analysis was calculated for $C_{16}H_{14}N_2O_5$:

Calculated: C: 61.14%; H: 4.49%; N: 8.91%; Found: C: 61.05%; H: 4.63%; N: 8.73%.

EXAMPLE 20

Performing the process as described in Example 1 but replacing the 1-(5'-nitrofuryl)-butane-1,3-dione with 1-(5'-nitrofuryl)-pentane-1,3-dione, the following 5-nitrofuryl quinolines were prepared:

a. 2-ethyl-4-[2'-(5'-nitrofuryl)]quinoline m.p. 127°–128°. The analysis was calculated for $C_{15}H_{12}N_2O_3$:

Calculated: C: 67.16%; H: 4.51%; N: 10.44%; Found: C: 67.42%; H: 4.70%; N: 10.27%.

The corresponding N-oxide has a m.p. of 184.5°–195.5° b. 2-ethyl-4-[2'-(5'-nitrofuryl)]-6-ethyl quinoline m.p. 117.5°–118.5°. The analysis was calculated for $C_{17}H_{16}N_2O_3$:

Calculated: C: 68.91%; H: 5.44%; N: 9.45%; Found: C: 69.09%; H: 5.56%; N: 9.37%.

The corresponding N-oxide was prepared, m.p. 173.5°–174.5°.

c. 2-ethyl-4-[2'-(5'-nitrofuryl)]-6-methyl quinoline m.p. 112.5°–113.5°. The analysis was calculated for $C_{16}H_{14}N_2O_3$:

Calculated: C: 68.08%; H: 5.00%; N: 9.92%; Found: C: 68.21%; H: 5.13%; N: 10.05%.

The corresponding N-oxide was prepared, m.p. 158.5°–159.5°.

Performing the process as described in Example 1 but replacing the 1-('nitrofuryl)-butane-1,3-dione with 1-(5'-nitrofuryl)-5-methylpentane-1,3-dione, the following 5-nitrofuryl quinolines were prepared:

a. 2-isopropyl-4-[2'-(5'-nitrofuryl)]-6-methyl quinoline; m.p. 94°–95°.

The corresponding N-oxide has a m.p. of 201°–202°.

b. 2-isopropyl-4-[2'-(5'-nitrofuryl)]-6-ethyl quinoline; m.p. 108°–109°.

The corresponding N-oxide has a m.p. of 146°–148°.

EXAMPLE 21

A mixture comprising 2 g of 2-methyl-4-[2'-(5'-nitrofuryl)]-7-hydroxy quinoline, prepared as described in Example 4, 40 ml of acetic anhydride and 1 ml of concentrated sulfuric acid were refluxed for 2 hours, then left to cool to room temperature and finally poured on ice water. After 2 hours of further stirring the brown crystals obtained were filtered off and washed throughly with water.

1.5 g of 2-methyl-4-[2'-5'-nitrofuryl)]-7-acetoxyquinoline were obtained., yield 65%.

An analytical sample was prepared by repeated recrystallisation from dioxane, nitromethane and isopropanol, mp. 171.5°–172.5°. The analysis was calculated for $C_{16}H_{12}N_2O_5$:

Calculated: C: 61.54%; H: 3.87%; N: 8.97%; Found: C: 61.37%; H: 3.83%; N: 9.01%.

The N-oxide of the above compound was prepared as described in previous examples, m.p. 176°.

EXAMPLE 22

19.7 g of 1-(5'-nitrofuryl)-2,4-butanedione and 13.7 g of m-phenetidine were heated for 20 minutes together with a catalytic amount of $ZnCl_2$ at 110°–120°. The mixture was then cooled and recrystallised from methanol to yield 28.5 g of 1-(5'-nitro-2'-furo)-butanone-3-(m-ethoxy-phenyl)imino, m.p. 129°–130°.

2 g of the above Schiff base were mixed with 25 g of polyphosphoric acid at about 5° C. The reaction mixture was a viscous mass which was heated for 10 minutes at 100°, then allowed to cool to room temperature and then 100 ml of water were added with external cooling. The pH was adjusted to 8, with ammonium hydroxide and the greenish crystals obtained were filtered off and washed with water. 1.7 g of the crude compound obtained, 2-methyl-4-[2'-(5'-nitrofuryl)]-7-ethoxy quinoline, were crystallised from ethanol 95%, m.p. 122.5°–123.5°.

An analytical sample was prepared by successive recrystallisation from isopropanol, acetone/water and cellosolve, m.p. 124.5°–126.5°.

The N-oxide of the above compound was prepared by oxidation with $H_2O_2$ (30%) in glacial acetic acid.

An analytical sample was prepared by repeated recrystallisations from nitromethane and ethanol, m.p. 201°–202°. The analysis was calculated for $C_{16}H_{14}N_2O_5$:

Calculated: C: 61.14%; H: 4.49%; N: 8.91%; Found: C: 60.99%; H: 4.61%; N: 8.84%.

EXAMPLE 23

A mixture of 2 g of 2-methyl-4-[2'-(5'-nitrofuryl)-]quinoline N-oxide, prepared as described in Example 1, and 10 g of acetic acid anhydride was heated to 120°–130° for 2 hours on an oil bath. The excess of acetic acid anhydride was then distilled off under reduced pressure and ice-water was added to the residue. Crystals precipitated which were separated by filtration and washed with water.

2.1 g of 2-acetoxymethyl-4-[2'-(5'-nitrofuryl)]quinoline were obtained; yield 89% m.p. 125°–130°. After recrystallisation from ethanol with charcoal the melting point rose to 135°–136°.

An analytic sample having a m.p. of 137°–138° was prepared. The analysis was calculated for $C_{16}H_{12}N_2O_5$ Calculated: C: 61.54%; H: 3.87%; N: 8.97%; Found: C: 61.44%; H: 3.92%; N: 9.00%.

The N-oxide of the above compound was prepared by oxidation with hydrogen peroxide dissolved in glacial acetic acid yielding a compound melting at 188°–189.5° after recrystallisation from isopropanol.

2-Hydroxymethyl-4-[2'-(5'-nitrofuryl)]quinoline was prepared by refluxing the 2-acetoxy-methyl-4-[2'-(5'-nitrofuryl)]quinoline in a 12% sulfuric acid solution.

EXAMPLE 24

In the same manner as described in Example 23 there was prepared from 2-methyl-4-[2'-(5'-nitrofuryl)]-7-hydroxyquinoline N-oxide the 2-acetoxymethyl-4-[2'-(5'-nitrofuryl)]-7-acetoxy quinoline, m.p. 151.5°–152°. The analysis was calculated for $C_{18}H_{14}N_2O_7$:

Calculated: C: 58.38%; H: 3.81%; N: 7.56%; Found: C: 58.41%; H: 4.04%; N: 7.72%.

EXAMPLE 25

In a 250 ml three-necked, round-bottomed flask, fitted with stirrer and reflux condenser, were placed 20 ml of diozane (90%) and 3.9 g of selenium dioxide. The mixture was heated to 50°–60° until the solid was dissolved. Then 5 g of 2-methyl-4-[2'-(5'-nitrofuryl)]quinoline (prepared as described in Example 1) were added to the solution in one lot and the resulting mixture was refluxed for 2 hours with continued stirring. The hot solution was then twice filtered with charcoal, and concentrated to ½ of its initial volume. The precipitated crystals of 4-[2'-(5'-nitrofuryl)]quinoline-2-carboxaldehyde, were then filtered off.

The crude compound was recrystallised from dioxane, yielding 4.2 g of a yellow compound, mp. 185°–187°.

The following compounds were obtained in a similar manner:

4-[2'-(5'-nitrofuryl)]-7-ethoxy quinoline-2-carboxaldehyde, m.p. 179°–181°;

4-[2'-(5'-nitrofuryl)]-7-chloro quinoline-2-carboxaldehyde, m.p. 148°–151°;

4-[2'-(5'-nitrofuryl)]-7-methyl quinoline-2-carboxaldehyde, m.p. 155°–157°;

4-[2'-(5'-nitrofuryl)]-6-methyl quinoline-2-carboxaldehyde, m.p. 110°–119°.

4-[2'-(5'-nitrofuryl)]-6-ethyl quinoline-2-carboxaldehyde m.p. 157°–161°.

Similarly from 2-ethyl-4-[2'-(5'-nitrofuryl)]quinoline there was prepared 4-[2'-(5'-nitrofuryl)]quinoline-2-methyl ketone, m.p. 209°–211°.

EXAMPLE 26

In a 100 ml three-necked, round-bottomed flask fitted with stirrer and reflux condenser, were placed 2.7 g of 4-[2'(5'-nitrofuryl)]quinoline-2-carboxaldehyde and 50 ml of dioxane. The mixture was heated to boiling until a clear solution was obtained. Then added at once 0.7 g hydroxylamine hydrochloride dissolved in 20 ml water. The mixture was refluxed with stirring for 2 hours. The hot solution was filtered with charcoal and concentrated to 1/5 of its initial volume. 50 ml of water were added and the crystaline precipitate was filtered off. 2.6 g of 4-[2'-(5'-nitrofuryl)]quinoline-2-carboxaldehyde oxime were obtained. Yield 92%, m.p. 202.5°–204°.

An analytical sample was obtained by successive recrystallisation from isopropanol, nitromethane and acetone, m.p. 208°–210°. The analysis was calculated for $C_{14}H_9N_3O_4$:

Calculated: C: 59.37%; H: 3.20%; N: 14.84%; Found: C: 59.23%; H: 3.33%; N: 14.68%.

The N-oxide of the above compound was prepared in the usual manner, i.e. by oxidation with $H_2O_2$ (30%) in glacial acetic acid, m.p. 201.5°–203.5°. The analysis was calculated for $C_{14}H_9N_3O_5$:

Calculated: C: 56.19%; H: 3.03%; N: 14.04%; Found: C: 56.33%; H: 3.17%; N: 13.94%.

EXAMPLE 27

In the same manner as described in Example 26 but replacing the hydroxylamine hydrochloride with semicarbazide hydrochloride there was obtained 4-[2'-(5'-nitrofuryl)]quinoline-2-carboxaldehyde semicarbazone.

An analytical sample was prepared by successive recrystallisation from isopropanol, acetone and dioxane, m.p. 247°–248°. The analysis was calculated for $C_{15}H_{11}N_5O_4$:

Calculated: C: 55.39%; H: 3.41%; N: 21.53%; Found: C: 55.54%; H: 4.03%; N: 21.34%.

In the same manner as described in Example 26, replacing the hydroxylamine hydrochloride with hydroxylethyl hydrazine there was obtained 4-[2'-(5'-nitrofuryl)]-quinoline-2-carboxaldehyde B-hydroxyethyl hydrazine; m.p. 143°–145°.

EXAMPLE 28

In the same manner as described in Example 26 but replacing the hydroxylamine hydrochloride with 1-amino-oxazolidine-2-one there was obtained 4-[2'-(5'-nitrofuryl)]quinoline-2-carboxaldehyde-amino-oxazolidone, mp. 264°–265.5°. The analysis was calculated for $C_{17}H_{12}N_4O_5$:

Calculated: C: 57.96%; H: 3.34%; N: 15.90%, Found: C: 57.83%; H: 3.45%; N: 15.93%.

EXAMPLE 29

In the same manner as described in Example 26 but replacing the hydroxylamine hydrochloride with 1-aminohydantoin there was obtained 4-[2'-(5'-nitrofuryl)]quinoline-2-carboxaldehyde aminohydantoin, m.p. 233°–235°.

Likewise in the same manner as described in Example 26 but replacing the hydroxylamine hydrochloride with acetylhydrazine, phenylhydrazine or isonicotinoyl hydrazine there were obtained acetyl hydrazone, phenylhydrazone and isonicotinoyl hydrazone, respectively, of the 4-[2'-(5'-nitrofuryl)]quinoline-2-carboxaldehyde.

EXAMPLE 30

4-[2'-(5'-nitrofuryl)]quinoline-2-carboxaldehyde prepared as described in Example 25 was oxidised with $H_2O_2$-glacial acetic acid to yield 2-carboxy-4-[2'-(5'-nitrofuryl)]quinoline, yield 85% m.p. crude 192°–196°; after recrystallisation from isopropanol, nitromethane the melting point was 199.5°–200°.

A mixed melting point determination with the compound prepared in Example 6 gave no depression.

The N-oxide was prepared, m.p. 188°–189°.

The 2-carboxy-4-[2'-(5'-nitrofuryl)]quinoline was treated with thionyl chloride (by a method known per se) to yield the corresponding acylchloride which in turn was treated with:

a. Abs.ethanol to yield 2-carbethoxy-4-[2'-(5'-nitrofuryl)]quinoline; m.p. 183.5°–184.5°.

b. diethylamine to yield 4-[2'-(5'-nitrofuryl)]quinoline-2-carboxylic acid diethylamide, m.p. 141.5°–142.5°.

c. morpholine to yield 2-carboxylic acid-N-morpholine amide-4-[2'-(5'-nitrofuryl)]-quinoline, m.p. 173.5°–177.5°.

The N-oxide was prepared; m.p. 232°–233°.

Other aldehydes, prepared as described in Example 25, were oxidized in the same manner to yield:

2-carboxy-4-[2'-(5'-nitrofuryl)]-7-ethoxy quinoline, m.p. 176°–177°;

2-carboxy-4-[2'-(5'-nitrofuryl)]-7-methyl quinoline, m.p. 203°–204°;

2-carboxy-4-[2'-(5'-nitrofuryl)]-7-ethoxy quinoline N-oxide, m.p. 178°–179°;

2-carboxy-4-[2'-(5'-nitrofuryl)]-7-chloro quinoline N-oxide, m.p. 177°–178°;

2-carboxy-4-[2'-(5'-nitrofuryl)]-7-methyl quinoline N-oxide m.p. 195°–196°;

2-carboxy-4-[2'-(5'-nitrofuryl)]-6-methyl quinoline N-oxide m.p. 183°–184°;

2-carboxy-4-[2'-(5'-nitrofuryl)]-6-ethyl quinoline N-oxide m.p. 169°–170°.

EXAMPLE 31

A mixture of

| | |
|---|---|
| Polyethylene glycol 4000 | 200 g |
| Polyethylene glycol 1500 | 200 g |
| Polyethylene glycol 300 | 250 g |
| Propylene glycol | 125 g |
| Cety alcohol | 20 g | was heated on a steam bath. 2–3 g of 2-methyl-4-[2'-(5'-nitrofuryl)]quinoline, prepared as described in Example 1, were added to the melt with efficient stirring. After cooling the mass obtained was passed through an ointment roller to produce an ointment.

EXAMPLE 32

16 g of 4-methyl-2-[2'-(5'-nitrofuryl)]quinoline, prepared as described in Example 2, and 25 g of lactose were mixed together. A starch mucilage binder was added in an amount sufficient to produce a proper mass for granulation. The mass obtained was passed through a sieve, dried at 70°–80° and then again passed through a sieve. A small quantity of talcum and starch powder was added and tablets were pressed in a tabletting machine.

EXAMPLE 33

A mixture of 1 g of 2-methyl-4-[2'-(5'-nitrofuryl)]-7-methoxy quinoline N-oxide, prepared as described in Example 7, 4 g of lactose, 6 g of calcium carbonate and 50 g of soyabean meal were mixed in a Fisher-Kendall mixer to be utilised as premix for animal feedstuffs.

EXAMPLE 34

9.85 g (0.05 moles) of 1-(5'-nitrofuryl)-butane-1,3 dione and 9 g (0.05 mole) of 4-amino-2-methoxyacetanilide were heated together at 110° C. with a pinch of $ZnCl_2$ as catalyst. A melt was obtained and after 20 minutes the whole mass solidified. It was kept a further 10 minutes at 110°–120°. After cooling and recrystallization from methanol, 16 g of crystalline Schiff base, 1-(5'-nitro-2'-furo)-butanone-3-(3''-methoxy-4''-acetylamino-phenyl) imino were obtained; m.p. 207°–210°, yield 89%.

7 g of the above Schiff base were admixed with 85 g of polyphosphoric acid at room temperature. The reaction mixture was a viscous mass which was heated for 40 minutes at 110°—110°, then allowed to cool to room temperature and then 300 ml of water were added with external cooling. The pH was adjusted with ammonium-hydroxide to 8 and the dark-colored crystals obtained were filtered off and washed with water. 6.25 g of the crude compound were obtained, 2-methyl-4-[2'-

(5'-nitrofuryl)]-6-acetylamino-7-methoxy-quinoline; m.p. 210°–216°.

An analytical sample was prepared by repeated crystallisations from isopropanol, benzene and nitromethane; m.p. 239°–240.5°. The analysis was calculated for $C_{17}H_{17}N_3O_5$:

Calculated: C: 59.47%; H: 4.99%; N: 12.24%; Found: C: 59.80%; H: 4.80%; N: 12.23%.

The N-oxide was prepared; m.p. 253°–256°.

EXAMPLE 35

7 g of 1-(5'-nitro-2'-furo)-butanone-3-(3''-methoxy-4''-acetylamino-phenyl)imino prepared as described in Example 34 were dissolved at about 5° in 20 ml of concentrated sulfuric acid. The clear solution was allowed to reach room temperature and was afterwards heated to 100°–110° for 10 minutes and then poured on ice water and neutralised with ammonia.

A red precipitate was obtained which was filtered off. 5 g of a crude compound were obtained, 2-methyl-4-[2'-(5'-nitrofuryl)]-6-amino-7-methoxy-quinoline.

An analytical sample was prepared by repeated recrystallisations from isopropanol, benzene, and nitromethane; m.p. 216°–217°. The analysis was calculated for $C_{15}H_{15}N_3O_4$:

Calculated: C: 59.80%; H: 5.02%; N: 13.95%; Found: C: 59.85%; H: 4.71%; N: 13.99%.

The N-oxide was prepared, m.p. 229°–230°.

EXAMPLE 36

In the same manner as described in Example 34, replacing the 4-amino-2-methoxy-acetanilide with 2,6-diaminotoluene there was prepared 2,6-dimethyl-4-[2'-(5'-nitrofuryl)]-7-amino-quinoline; m.p. 176°–177°.

This compound was acetylated to yield 2,6-dimethyl-4-[2'-(5'-nitrofuryl)]-7-acetylaminoquinoline; m.p. 257°–258.5°.

By another acetylation there was obtained 2,6-dimethyl-4-[2'-(5'-nitrofuryl)]-7-trifluoro-acetylamino quinoline; m.p. 211°–211.5°.

EXAMPLE 37

2-carboxy-4-[2'-(5'-nitrofuryl)]quinoline, obtained as described in Example 6 or 30, was heated in a high boiling solvent, diphenyl ether, to 175°–180° for 5 hours. After cooling the solution was poured on water, the precipitate was filtered off and dried to yield 4-[2'-(5'-nitrofuryl)]quinoline, m.p. 176°–177°. The N-oxide was prepared, m.p. 185°–186°.

EXAMPLE 38

In the same manner as described in Example 25 there was prepared from 2-methyl-4-[2'-(5'-nitrofuryl)]-7-methoxy-quinoline the 4-[2'-(5'-nitrofuryl)]-7-methoxy quinoline-2-carboxaldehyde, m.p. 203.5°–204.5°.

The compound obtained was oxidised, in the same manner as described in Example 30, with $H_2O_2$ in glacial acetic acid to yield 2-carboxy-4-[2'-(5'-nitrofuryl)]-7-methoxy quinoline N-oxide; m.p. 192°–193°.

The compound obtained was heated in 50 ml of boiling DMF for 30 minutes and then treated as described in Example 30 to yield 4-[2'-(5'-nitrofuryl)]-7-methoxy quinoline N-oxide; m.p. 209°–210°.

Following the procedure of Example 37, and utilising as starting materials the carboxy compounds of Example 30, the following compounds were prepared:
4-[2'-(5'-nitrofuryl)]-7-ethoxy quinoline, m.p. 142°–144°;
4-[2'-(5'-nitrofuryl)]-7-ethoxy quinoline N-oxide, m.p. 185°–187°;
4-[2'-(5'-nitrofuryl)]-7-chloro quinoline N-oxide, m.p. 220°–221°;
4-[2'-(5'-nitrofuryl)]-7-methyl quinoline N-oxide, m.p. 194°–195°;
4-[2'-(5'-nitrofuryl)]-6-methyl quinoline N-oxide, m.p. 183°–184°;
4-[2'-(5'-nitrofuryl)]-6-ethyl quinoline N-oxide, m.p. 185°–186°.

We claim:

1. A nitrofuryl quinoline of the formula:

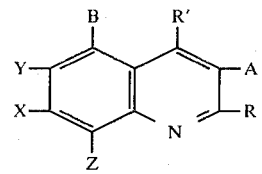

in which R is hydrogen, 5-nitrofuryl, lower alkyl, halo-substituted lower alkyl, lower alkanoyloxy-lower alkyl, lower alkoxy or hydroxy-lower alkyl; R' is hydrogen, 5-nitrofuryl or lower alkyl; X is hydrogen, halogen, hydroxy, lower alkoxy, or lower alkyl; Y is hydrogen or lower alkyl; Z is hydrogen, nitro, lower alkyl or lower alkoxy; A is hydrogen or lower alkyl; B is hydrogen, lower alkyl, nitro or lower alkoxy; or X and Y taken together complete a benzene nucleus; at least one of substituents R and R' being a 2-(5-nitrofuryl) group; wherein A, B, X, Y and Z are non-tertiary lower alkyl when adjacent to groups other than hydrogen; and when X is hydroxy, R, R', B and Z are not lower alkoxy; and their nitrogen oxides and non-toxic acid addition salts.

2. A nitrofuryl quinoline derivative according to claim 1 which is the compound 2-[2'-(5'-nitrofuryl)]-4-methyl quinoline or its N-oxide.

3. A nitrofuryl quinoline derivative according to claim 1 which is the compound 2-methyl-4-[2'-(5'-nitrofuryl)]-7-chloro quinoline or its N-oxide.

4. A nitrofuryl quinoline derivative according to claim 1 which is the compound 2-methyl-4-[2'-(5'-nitrofuryl)]-7-hydroxy quinoline or its N-oxide.

5. A nitrofuryl quinoline derivative according to claim 1 which is the compound 2-tribromomethyl-4-[2'-(5'-nitrofuryl)]quinoline.

6. A nitrofuryl quinoline derivative according to claim 1 which is the compound 2-methyl-4-[2'-(5'-nitrofuryl)]-7-methoxy quinoline or its N-oxide.

7. A nitrofuryl quinoline derivative according to claim 1 which is the compound 2-methyl-4-[2'-(5'-nitrofuryl)]-6-methyl quinoline or its N-oxide.

8. A nitrofuryl quinoline derivative according to claim 1 which is the compound 2-methyl-4-[2'-(5'-nitrofuryl)]-7-chloro-8-nitroquinoline.

9. A nitrofuryl quinoline derivative according to claim 1 which is the compound 2,8-dimethyl-4-[2'-(5'-nitrofuryl)]quinoline or its N-oxide.

10. A nitrofuryl quinoline derivative according to claim 1 which is the compound 2,7-dimethyl-4-[2'-(5'-nitrofuryl)]quinoline or its N-oxide.

11. A nitrofuryl quinoline derivative according to claim 1 which is the compound 2-dibromomethyl-4-[2'-(5'-nitrofuryl)]quinoline.

12. A nitrofuryl quinoline derivative according to claim 1 which is the compound 2-trichloromethyl-4-[2'-(5'-nitrofuryl)]quinoline.

13. A nitrofuryl quinoline derivative according to claim 1 which is the compound 2-tribromomethyl-4-[2'-(5'-nitrofuryl)]-6-methyl quinoline.

14. A nitrofuryl quinoline derivative according to claim 1 which is the compound 2-[2'-(5'-nitrofuryl)]quinoline or its N-oxide.

15. A nitrofuryl quinoline derivative according to claim 1 which is the compound 2-[2'-(5'-nitrofuryl)]-3-methyl quinoline.

16. A nitrofuryl quinoline derivative according to claim 1 which is the compound 2-methyl-4-[2'-(5'-nitrofuryl)]-5-nitro quinoline.

17. A nitrofuryl quinoline derivative according to claim 1 which is the compound 2-methyl-4-[2'-(5'-nitrofuryl)]-8-nitro quinoline.

18. A nitrofuryl quinoline derivative according to claim 1 which is the compound 2,8-dimethyl-4-[2'-(5'-nitrofuryl)]-5-nitro quinoline.

19. A nitrofuryl quinoline derivative according to claim 1 which is the compound 2-methyl-4-[2'-(5'-nitrofuryl)]-6-ethyl quinoline or its N-oxide.

20. A nitrofuryl quinoline derivative according to claim 1 which is the compound 2,6,8-trimethyl-4-[2'-(5'-nitrofuryl)]quinoline.

21. A nitrofuryl quinoline derivative according to claim 1 which is the compound 2,5,8-trimethyl-4-[2'-(5'-nitrofuryl)]quinoline.

22. A nitrofuryl quinoline derivative according to claim 1 which is the compound 2-methyl-4-[2'-(5'-nitrofuryl)]-5,8-dimethoxy quinoline.

23. A nitrofuryl quinoline derivative according to claim 1 which is the compound 2-ethyl-4-[2'-(5'-nitrofuryl)]quinoline or its N-oxide.

24. A nitrofuryl quinoline derivative according to claim 1 which is the compound 2-ethyl-4-[2'-(5'-nitrofuryl)]-6-ethyl quinoline or its N-oxide.

25. A nitrofuryl quinoline derivative according to claim 1 which is the compound 2-ethyl-4-[2'-(5'-nitrofuryl)]-6-methyl quinoline or its N-oxide.

26. A nitrofuryl quinoline derivative according to claim 1 which is the compound 2-methyl-4-[2'-(5'-nitrofuryl)]-7-ethoxy quinoline or its N-oxide.

* * * * *